(12) United States Patent
Vogt et al.

(10) Patent No.: US 11,490,940 B2
(45) Date of Patent: *Nov. 8, 2022

(54) DEVICE FOR THE MIXING AND STORING OF POLYMETHYLMETHACRYLATE BONE CEMENT

(71) Applicant: HERAEUS MEDICAL GMBH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 1053 days.

This patent is subject to a terminal disclaimer.

(21) Appl. No.: 16/034,618

(22) Filed: Jul. 13, 2018

(65) Prior Publication Data
US 2018/0317991 A1    Nov. 8, 2018

Related U.S. Application Data

(62) Division of application No. 14/825,483, filed on Aug. 13, 2015, now Pat. No. 10,045,806.

(30) Foreign Application Priority Data

May 4, 2015    (DE) ...................... 10 2015 106 899.0

(51) Int. Cl.
*A61B 17/88*    (2006.01)
*B01F 31/40*    (2022.01)
(Continued)

(52) U.S. Cl.
CPC .......... *A61B 17/8833* (2013.01); *B01F 31/40* (2022.01); *B01F 33/5012* (2022.01);
(Continued)

(58) Field of Classification Search
CPC ............ A61B 17/8833; A61B 17/8802; A61B 2017/8838; B01F 13/0023; B01F 13/003; B01F 13/06; B01F 15/0206
(Continued)

(56) References Cited

U.S. PATENT DOCUMENTS 3,390,814 A    2/1968  Creighton
4,671,263 A    6/1987  Draenert
(Continued)

FOREIGN PATENT DOCUMENTS

DE    36 40 279 A1    6/1987
DE    20005333 U1    7/2001
(Continued)

OTHER PUBLICATIONS

Canadian Office Action for corresponding Canadian Application No. 2,900,121 dated Jul. 4, 2016.
(Continued)

*Primary Examiner* — Marc C Howell
(74) *Attorney, Agent, or Firm* — Norris McLaughlin, P.A.

(57) ABSTRACT

Device for the mixing of polymethylmethacrylate bone cement and for storing a monomer liquid and a cement powder as starting components of the bone cement, comprising
a cartridge having an internal space closed on one side by a mobile dispensing plunger;
a monomer container for a monomer liquid and/or a connector for attachment of a monomer container which can be opened in the device so that the monomer liquid flows from the monomer container into the device; and
a connecting conduit through which the monomer liquid can be guided into the internal space of the cartridge; having a pumping plunger that can be shifted axially in
(Continued)

the hollow cylinder arranged in the hollow cylinder, which can be used to push monomer liquid from the hollow cylinder through the connecting conduit into the internal space of the cartridge by actuating the pumping plunger.

28 Claims, 7 Drawing Sheets

(51) Int. Cl.
  *B01F 33/70* (2022.01)
  *B01F 33/501* (2022.01)
  *B01F 35/71* (2022.01)
  *B01F 35/75* (2022.01)
  *B01F 101/20* (2022.01)

(52) U.S. Cl.
  CPC ........ *B01F 33/50112* (2022.01); *B01F 33/70* (2022.01); *B01F 35/7131* (2022.01); *B01F 35/7174* (2022.01); *B01F 35/754251* (2022.01); *A61B 2017/8838* (2013.01); *B01F 2101/20* (2022.01)

(58) Field of Classification Search
  USPC .......................................... 366/130, 139, 189
  See application file for complete search history.

(56) References Cited

U.S. PATENT DOCUMENTS

| | | | |
|---|---|---|---|
| 4,758,096 | A | 7/1988 | Gunnarsson |
| 4,889,432 | A | 12/1989 | Paiierson |
| 4,973,168 | A | 11/1990 | Chan |
| 5,100,241 | A | 3/1992 | Chan |
| 5,344,232 | A | 9/1994 | Nelson et al. |
| 5,551,778 | A | 9/1996 | Hauke et al. |
| 5,586,821 | A | 12/1996 | Bonitati et al. |
| 5,588,745 | A | 12/1996 | Tanaka et al. |
| 5,624,184 | A | 4/1997 | Chan |
| 5,674,394 | A | 10/1997 | Whitmore |
| 5,901,883 | A | 5/1999 | Ritsche |
| 5,997,544 | A | 12/1999 | Nies et al. |
| 6,033,105 | A | 3/2000 | Barker et al. |
| 6,296,149 | B1 | 10/2001 | Long |
| 6,709,149 | B1 | 3/2004 | Tepic |
| 7,073,936 | B1 | 7/2006 | Jonsson |
| 7,175,336 | B2 | 2/2007 | Voellmicke et al. |
| 8,308,340 | B2 | 11/2012 | Ferrante et al. |
| 8,662,736 | B2 | 3/2014 | Vogt et al. |
| 8,757,866 | B2 | 6/2014 | Vogt et al. |
| 8,926,623 | B2 | 1/2015 | Trieu et al. |
| 8,944,107 | B2 | 2/2015 | Greter et al. |
| 8,992,071 | B2 | 3/2015 | Vogt |
| 9,010,586 | B2 | 4/2015 | Vogt et al. |
| 9,132,573 | B2 | 9/2015 | Vogt et al. |
| 9,694,514 | B2 | 7/2017 | Vogt |
| 2001/0016703 | A1 | 8/2001 | Wironen et al. |
| 2002/0058908 | A1 | 5/2002 | Zierenberg et al. |
| 2004/0167617 | A1 | 8/2004 | Voellmicke et al. |
| 2010/0329074 | A1 | 12/2010 | Vogt et al. |
| 2011/0273954 | A1 | 11/2011 | Greter et al. |
| 2012/0006874 | A1 | 1/2012 | Vogt et al. |
| 2012/0026825 | A1 | 2/2012 | Vogt et al. |
| 2013/0135959 | A1 | 5/2013 | Vogt et al. |
| 2015/0367301 | A1 | 12/2015 | Vogt |

FOREIGN PATENT DOCUMENTS

| | | |
|---|---|---|
| DE | 698 12 726 T2 | 2/2004 |
| DE | 60218464 T2 | 11/2007 |
| DE | 10 2009 031178 B3 | 9/2010 |
| DE | 10 2010 026 496 B4 | 5/2014 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| EP | 1 466 572 A2 | 10/2004 |
| WO | 94/26403 A1 | 11/1994 |
| WO | 99/67015 A1 | 12/1999 |
| WO | 00/35506 A1 | 6/2000 |
| WO | 2006058153 A1 | 6/2006 |

OTHER PUBLICATIONS

Japanese Office Action and English Translation for corresponding Japanese Application No. 2015-195667 dated Aug. 30, 2016.
Taiwanese Office Action and English Translation for corresponding Taiwanese Application No. 104127989 dated Jan. 17, 2017.
European Search Report for corresponding EP Application No. 15180189.1 dated Oct. 17, 2016.

DEVICE FOR THE MIXING AND STORING OF POLYMETHYLMETHACRYLATE BONE CEMENT

This application is a division of application Ser. No. 14/825,483, filed Aug. 13, 2015, now pending, claiming priority of German Application 10 2015 106 899.0 filed May 4, 2015.

The invention relates to a mixing system for the mixing of polymethylmethacrylate bone cement (PMMA bone cement) from two starting components, in particular for the mixing of a medical bone cement, and for storage of the starting components.

The invention further relates to a method for the mixing of polymethylmethacrylate bone cement.

Accordingly, the subject matter of the invention is a device for the storing and mixing of polymethylmethacrylate bone cement as well as method(s) for the mixing of polymethylmethacrylate bone cement.

BACKGROUND OF THE INVENTION

Polymethylmethacrylate (PMMA) bone cements are based on the pioneering work of Sir Charnley (Charnley, J.: Anchorage of the femoral head prosthesis of the shaft of the femur. J. Bone Joint Surg. 42 (1960) 28-30.). PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, a radiopaquer, and the initiator dibenzoylperoxide. The polymers of the powder component are produced on the basis of methylmethacrylate and comonomers, such as styrene, methylacrylate or similar monomers by means of polymerisation, preferably by suspension polymerisation. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Methylmethacrylate is the monomer used most commonly in polymethylmethacrylate bone cements. Redox initiator systems usually consist of peroxides, accelerators and, if applicable, suitable reducing agents. Radicals are formed only if all ingredients of the redox initiator systems act in concert. For this reason, the ingredients of the redox initiator system in the separate starting components are arranged appropriately such that these cannot trigger a radical polymerisation. The starting components are stable during storage provided their composition is adequate. Only when the two starting components are mixed to produce a cement dough, the ingredients of the redox initiator system, previously stored separately in the two pastes, liquids or powders react with each other forming radicals which trigger the radical polymerisation of the at least one monomer. The radical polymerisation then leads to the formation of polymers while consuming the monomer, whereby the cement dough is cured.

PMMA bone cements can be mixed by mixing the cement powder and the monomer liquid in suitable mixing beakers with the aid of spatulas. It is a disadvantage of this procedure that air inclusions may arise and/or be present in the cement dough thus formed and may have an adverse influence on the mechanical properties of the cured bone cement and may therefore cause destabilisation of the bone cement later on.

A multitude of vacuum cementing systems has been proposed to prevent air inclusions in bone cement dough, some of which are listed in the following for exemplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A. In the vacuum cementing systems thus specified, there is a need to connect an external vacuum pump to generate the negative pressure. These are generally operated by compressed air utilising the Venturi principle. The compressed air required for operation of the vacuum pumps is supplied either by stationary compressed air facilities or by electrically-operated compressors. In addition, it is also feasible to use electrically-operated vacuum pumps to generate vacuum.

Cementing systems, in which both the cement powder and the monomer liquid are already packed in separate compartments of the mixing systems and are mixed with each other in the cementing system only right before application of the cement, are a development of cementing technology. Said closed full-prepacked mixing systems were proposed through EP 0 692 229 A1, DE 10 2009 031 178 B3, U.S. Pat. No. 5,997,544 A, U.S. Pat. No. 6,709,149 B1, DE 698 12 726 T2, and U.S. Pat. No. 5,588,745 A. Said mixing systems also require an external vacuum source.

Patent DE 10 2009 031 178 B3 discloses a generic mixing system having a two-part dispensing plunger for closure of a cement cartridge. A combination of a gas-permeable sterilisation plunger and a gas-impermeable sealing plunger is used in this context. This principle of a closed vacuum mixing system is implemented in the closed cementing system, PALACOS® PRO, made and distributed by Heraeus Medical GmbH.

WO 00/35506 A1 proposes a device, in which the polymethylmethacrylate bone cement powder is stored in a cartridge, whereby the cement powder fills the entire volume of the cartridge and the volume of the intervening spaces between the particles of the cement powder correspond to the volume of the monomer liquid required for production of bone cement dough with the cement powder stored in the cartridge. The design of said device is such that the monomer liquid is supplied into the cartridge from above by the action of a vacuum, whereby a vacuum is applied to a vacuum connector on the underside of the cartridge for this purpose. As a result, the monomer liquid is drawn through the cement powder, whereby the air situated in the intervening space of the cement particles is replaced by the monomer liquid. This does not include a mechanical mixing of the cement dough thus formed by means of a stirrer.

It is a disadvantage of this system that cement powders that swell rapidly in the presence of the monomer liquid cannot be mixed with this device because the rapidly swelling cement powder particles form a gel-like barrier of approximately 1 to 2 cm after ingress of the monomer liquid into the cement powder and impede the migration of the monomer liquid through the entire cement powder. Moreover, exposed to the action of a vacuum, it cannot be excluded that the monomer liquid is aspirated through the vacuum connector after the monomer liquid fully penetrates into the cement powder. In this case, an insufficient amount of monomer liquid is available for curing by means of radical polymerisation and/or the mixing ratio, and therefore the consistency of the bone cement, is changed inadvertently. Moreover, it is a problem that the air enclosed between the cement powder particles is to be displaced from top to bottom by the monomer liquid, because the air, having a lower specific weight as compared to the monomer liquid, tends to migrate upwards in the cement powder and not downwards in the direction of the vacuum connector.

If vacuum mixing systems are used for cementing, external vacuum pumps need to be provided. Said vacuum pumps are expensive and need to be cleaned after use. Moreover, vacuum hoses for connecting the vacuum pumps to the vacuum mixing systems are required. Said vacuum hoses need to be enclosed with the vacuum mixing systems. Accordingly, prior to the mixing using a vacuum mixing system, the vacuum pump needs to be set-up in the surgical theatre (OR) and must be connected to an energy source, such as compressed air or electrical power. Then, the vacuum pump is connected to the vacuum mixing system by means of a vacuum hose. Said installation steps take up costly OR time and are potentially error-prone. The vacuum pump and connecting conduits to the vacuum mixing system and to external energy sources and supply conduits take up space and are potential tripping hazards and stumbling blocks that can disturb the often hectic procedure during a surgery.

An interesting concept has been proposed through EP 1 886 647 A1. Here, the cement powder is stored in an evacuated cartridge and the monomer liquid is situated in a separate container. The cartridge, which is kept at a negative pressure, being opened causes the monomer liquid to be aspirated into the cartridge without any ingress of air. A bone cement dough free of air inclusions is thus produced. Said concept requires the cartridge to remain closed in vacuum-tight manner during the storage before use such that no non-sterile air can enter into the cartridge. For this purpose, the cartridge must be sealed in a stable hermetic manner. Accordingly, one associated disadvantage is that the design is quite elaborate and that the content of the cartridge cannot be mixed by an externally-operated mixing system after aspiration of the monomer liquid since a feed-through for a mixing rod or a mixing tube would not readily be permanently vacuum-tight. All full-prepacked mixing systems known to date utilise a vacuum or a negative pressure to transfer the monomer liquid into the cement powder.

Accordingly, it is the object of the invention to overcome the disadvantages of the prior art. Specifically, the disadvantages of the known vacuum mixing systems having an external vacuum source are to be overcome. One of the objects of the invention is to develop a simple, closed device, in which polymethylmethacrylate bone cement powder (cement powder) and monomer liquid can be stored in separate compartments and can be mixed subsequently. It shall be possible for medical users to combine and mix the polymethylmethacrylate bone cement powder and the monomer liquid inside the device without the medical user being exposed to either of the two cement components. Any contact of the medical user with the polymethylmethacrylate bone cement powder and with the monomer liquid shall be excluded to the extent possible. The device to be developed is a full-prepacked mixing system. The device shall be designed appropriately such that the monomer liquid can be transferred into the polymethylmethacrylate bone cement powder without the use of external vacuum pumps driven by compressed air or compressors. Moreover, it is important that the device is functional in the absence of external energy sources, such as compressed air, vacuum or electrical current, even under the simplest external conditions and that it reliably ensures the production of bone cement dough. It shall be possible to use the device autonomously without additional technical equipment.

It is another object of the invention to provide a device, which makes it possible to specifically control the volume of monomer liquid that is transferred into the cement dough, such that the ratio of the volume of monomer liquid to the amount of cement powder can be varied in order to control the consistency and thus the processing properties of the bone cement.

Moreover, a method is to be provided that enables a monomer transfer and a mixing in full-prepacked mixing systems. In this context, the mixing system to be developed shall be manufactured mainly from inexpensive plastics.

Moreover, a device that is inexpensive to manufacture and working reliably for the mixing of a medical cement and, if applicable, for storage of the starting components of the cement, and a method for the mixing of the bone cement is to be devised, in which a simple manual operation can be used to mix the starting components, if possible without having to use an external or additional energy source and without air inclusions arising in the mixing material.

The main component of the polymethylmethacrylate bone cement, as mixing material, shall be a powder and the second component shall be present in the form of a liquid. Preferably, it shall be possible to store the two starting components of the bone cement separate from each other in the full-prepacked mixing system and to combine them safely through the use of the device.

SUMMARY OF THE INVENTION

The objects of the invention are met by a device for the mixing of polymethylmethacrylate bone cement (PMMA bone cement) and for storing the starting components of the bone cement, in particular a monomer liquid and a cement powder as starting components of the bone cement, whereby the device comprises
1) a cartridge having an internal space for mixing the bone cement, which is closed on one side by a mobile dispensing plunger;
2) a monomer container for a monomer liquid and/or a connector for attachment of a monomer container for a monomer liquid, such that the monomer container can be opened appropriately in the device such that the monomer liquid flows from the monomer container into the device;
3) a connecting conduit through which the monomer liquid can be guided into the internal space of the cartridge; whereby
4) a hollow cylinder is connected to the connecting conduit and the hollow cylinder is arranged between the monomer container or the connector for the monomer container and the internal space of the cartridge, whereby a pumping plunger that can be shifted axially in the hollow cylinder is arranged in the hollow cylinder, whereby the monomer liquid can flow from the opened monomer container into the hollow cylinder and the connecting conduit appropriately connects the hollow cylinder to the internal space of the cartridge, such that the pumping plunger can be used to push monomer liquid from the hollow cylinder through the connecting conduit into the internal space of the cartridge by actuating the pumping plunger.

DETAILED DESCRIPTION

The hollow cylinder being arranged between the monomer container for the monomer liquid or the connector for the monomer container and the cartridge does not mean that the hollow cylinder is geometrically arranged in between these, but rather that it is arranged between the monomer container or the connector for the monomer container and the cartridge with respect to the fluid connections, i.e. the flow direction of the monomer liquid, when the monomer liquid flows and/or is being pumped from the opened monomer container in the direction of the cartridge.

For the monomer liquid to flow from the opened monomer container into the hollow cylinder, the opened monomer container is connected to the hollow cylinder for this purpose, preferably is connected to the hollow cylinder by means of a confluence.

For the monomer liquid to be able to flow without the action of an additional force, the device must be set up according to the intended purpose such that gravitation effects the desired flow direction. Accordingly, the terms top and bottom as well as above and below and highest and lowest used in the scope of the present invention shall always be understood to relate to the set up of the device according to the intended purpose.

The internal space of the cartridge preferably has a cylindrical geometry. The cylindrical shape is the simplest shape by means of which the internal space of the cartridge and the hollow cylinder can be implemented. A cylindrical internal shape shall be understood geometrically to mean a general cylinder with any footprint, i.e. not just a cylinder with a circular footprint. Accordingly, the internal wall the internal space can be a cylinder with any footprint and the jacket of the hollow cylinder can be a cylinder with any footprint, i.e. including a non-circular or circular footprint. However, a cylindrical geometry with a rotationally symmetrical footprint footprint is preferred according to the invention.

To achieve a good pumping effect and to prevent leakage of monomer liquid from the pumping plunger, the pumping plunger closes in fluid-tight manner with respect to the internal walls of the hollow cylinder. For this purpose, a circumferential seal can be provided that closes off the pumping plunger with respect to the internal walls of the hollow cylinder.

According to the invention, it is preferred to have the monomer container be attached to the connector for the monomer container or to have the monomer container be inserted into the connector for the monomer container.

Preferably, the polymethylmethacrylate bone cement is mixed and/or can be produced from at least two components. Particularly preferably, one component is liquid (the monomer liquid) and the other component is powdered.

According to the invention, the starting components for the mixing material, in particular for the PMMA bone cement, are already present in the cartridge and the monomer container.

It is preferred, according to the invention, that the device is also well-suited for storage of the starting components, in particular when the containers are inserted into the device or the containers are a fixed part of the device.

The invention proposes to arrange in the cartridge a mixing facility that can be operated from outside, whereby the mixing facility preferably can be operated by means of a mixing rod that is guided through a feed-through in the dispensing plunger into the inside of the cartridge and is supported as in a bearing such as to be mobile.

Particularly preferably, the mixing rod can be rotated in the feed-through and is supported as in a bearing such as to be shiftable in longitudinal direction. By means of the mixing facility, the content of the internal space of the cartridge can be mixed conveniently by means of the mixing rod. Referring to the use of low viscosity bone cements, it is possible to forgo the use of a mixing rod and a mixing facility, since the monomer liquid displaces the air of the pore spaces between the cement powder particles and wets the cement powder particles before the cement powder swells.

The invention can just as well provide the dispensing plunger to be impermeable for powder, whereby it is preferred to have a pore filter that is permeable for gas and impermeable for powder arranged in the dispensing plunger.

The pore filtering can preferably provided as a pore disk. The impermeability for powder can prevent the cement powder from leaking from the inside of the cartridge. If the dispensing plunger is gas-permeable, the internal space can be evacuated and sterilised with a gas, such as, for example, ethylene oxide, through the dispensing plunger.

The invention also proposes the cement powder to be contained in the internal space of the cartridge.

The invention can just as well provide the monomer liquid to be contained in the monomer container. As a result, the device forms a ready-made full-prepacked mixing system that does not need to be filled with the cement powder prior to application. The cement powder is stored in the cartridge separate from the monomer liquid prior to use.

Moreover, the invention can provide a filter that is impermeable for the cement powder and permeable for the monomer liquid to be arranged between the connecting conduit and the internal space of the cartridge.

The cement powder can be prevented by this means from penetrating into the connecting conduit and from polymerising in this space when the monomer liquid is supplied and from inadvertently clogging and/or agglutinating the connecting conduit.

According to a further development, the present invention can provide the device to comprises a base, in which at least a part of the connecting conduit is arranged, whereby the cartridge is connected to the base in detachable manner, in particular is connected to the base in detachable manner by means of a screw thread, whereby, if applicable, the cement powder-impermeable and monomer liquid-permeable filter preferably is arranged in the base of the device, particularly preferably is arranged in the connection to the cartridge of the base.

As a result, the device can be set up and operated easily.

In this context, the invention can provide the hollow cylinder and the monomer container or the hollow cylinder and the connector for attachment of the monomer container to be connected to the base, preferably to be connected to the base in non-detachable manner.

This enables a particularly simple and inexpensive design of the device.

Preferred embodiments of the present invention can provide the monomer container for the monomer liquid or the connector for attachment of the monomer container to terminate in the hollow cylinder on a jacket surface of the hollow cylinder, preferably to terminate in the hollow cylinder right below the pumping plunger.

It can be insured by this means that all of the monomer liquid can flow into the hollow cylinder and can fill the hollow cylinder. Moreover, air can exit particularly easily from the hollow cylinder in this location.

Moreover, the invention can provide the device to comprise an opening means for opening of the monomer container by means of which the monomer container can be opened inside the device, whereby it is preferred to have a sieve or a filter arranged in the connection to the hollow cylinder by means of which fragments or shreds of the opened monomer container can be retained.

It can be preferable in this context to provide the monomer container to be a breakable glass ampoule.

The opening means being a part of the device allows the device to be used for storage of the monomer in the long-term as well. A suitable opening means is known, for example from patent DE 10 2010 026 496 B4.

A refinement of the invention involving the utilisation of gravitation to drive the flow of the monomer liquid into the hollow cylinder proposes the monomer container to be arranged above the connection to the hollow cylinder.

As a result, gravitation causes the monomer liquid to flow from the monomer container into the hollow cylinder after the monomer container has been opened. Alternatively, the monomer might as well be squeezed out and thus flows into the hollow cylinder.

Preferable devices can just as well be characterised in that the connecting conduit is connected to the hollow cylinder on the lower side, preferably is connected to the hollow cylinder at the lowest point of the hollow cylinder, whereby it is particularly preferred to have the pumping plunger be arranged on the opposite side of the hollow cylinder.

As a result, all of the monomer liquid can flow out and/or be squeezed from the pumping plunger.

The invention further proposes that the hollow cylinder comprises, on the side opposite from the pumping plunger, a floor that is conical, semi-spherical or tapering downwards in any other way, whereby the surface of the pumping plunger facing the floor of the hollow cylinder preferably forms a negative image of the floor.

As a result, all of the monomer liquid can flow out and/or be squeezed from the pumping plunger. This means that the entire monomer liquid flows to the lowest point of the hollow cylinder and no "dead" spaces are present, in which monomer liquid stays behind upon actuation of the pumping plunger. Due to the adaptation of the shape of the pumping plunger to the internal shape of the hollow cylinder, the entire monomer liquid is pressed by the pumping plunger from the hollow cylinder in the direction of the opening towards the connecting conduit upon a motion of the pumping plunger without any residues of the monomer liquid remaining in the hollow cylinder. Moreover, the front face of the pumping plunger have said conical or spherical and/or matching shape ensures that the air above the monomer liquid in the hollow cylinder can escape through the opening in the jacket surface of the hollow cylinder when the pumping plunger moves downwards and/or in the direction of the base, and no air bubbles remain above the monomer liquid during the transfer of monomer liquid into the internal space of the cartridge and/or into the cement powder.

Preferred embodiments can provide that the pumping plunger can be moved axially in the hollow cylinder by hand, preferably can be pressed axially into the hollow cylinder by hand.

As a result, it is feasible to press the monomer liquid from the hollow cylinder by hand and to transfer it to the internal space of the cartridge.

To simplify the operation and to provide for more variability of devices according to the invention, the invention can just as well provide the hollow cylinder to be transparent and to comprise markings indicating the filling level of a liquid in the hollow cylinder.

By this means, an amount of the monomer liquid that is determined by the markings can be filled into the hollow cylinder and/or can be pressed from the hollow cylinder into the internal space of the cartridge. This affords the option to use the device to produce a bone cement dough whose consistency is given by the amount of the monomer. Alternatively, the hollow cylinder can just as well not be transparent and markings can be provided on the end of the pumping plunger that project from the hollow cylinder in order to enable a defined advancement of the pumping plunger and to thus be able to press a defined volume of the monomer liquid from the hollow cylinder. Accordingly, with designs of this type it is feasible to either press the entire volume of the monomer liquid from the hollow cylinder into the cement powder in the internal space of the cartridge as well as to transfer only certain part-volumes of the monomer liquid from the hollow cylinder into the cement powder. By this means, the ratio of monomer liquid to amount of powder can be adjusted, which allows the period of time until the cement dough thus formed becomes non-tacky as well as the viscosity of the bone cement to be controlled specifically.

The invention can just as well provide the hollow cylinder to comprise an internal thread and the pumping plunger to comprise a matching external thread such that the pumping plunger can be screwed into the hollow cylinder in order to press the monomer liquid from the hollow cylinder into the internal space of the cartridge.

This also allows a defined amount of the monomer liquid to be pressed from the hollow cylinder into the internal space of the cartridge. This affords the option to use the device to produce a bone cement dough whose consistency is determine by the amount of the monomer liquid.

Alternatively, the invention can provide the device to comprise a tensioned compression spring and a locking mechanism, whereby the compression spring and/or the pumping plunger is or are locked by the locking mechanism in releasable manner, whereby the compression spring, when the locking mechanism is released, exerts a pressure on the pumping plunger to the effect that the pumping plunger is pressed into the hollow cylinder.

Analogously, in the embodiment, in which the hollow cylinder comprises an internal thread and the pumping plunger comprises an external thread, the invention can provide a tensioned rotary spring that screws the pumping plunger into the hollow cylinder after the locking mechanism is released.

These measures are advantageous in that they simplify the operation of the device. Moreover, possible incorrect operation can thus be prevented.

Moreover, the invention can provide the dispensing plunger to be connected to the cartridge by means of a releasable snap-in device, whereby the snap-in device can be released manually, in particular by the action of an axial force, such that the dispensing plunger can be moved axially in the internal space of the cartridge.

By this means, an inadvertent motion of the dispensing plunger, such as may be caused, for example, by a vacuum in the internal space of the cartridge, can be prevented.

To prevent the internal space of the cartridge from being filled with monomer liquid inadvertently, the invention can provide the connecting conduit between the hollow cylinder and the internal space of the cartridge to comprise a loop that points upwards, whereby the topmost point of the loop is situated above the junction of the monomer container or of the connector for the monomer container into the hollow cylinder.

By this means, the monomer liquid can be prevented from reaching the internal space of the cartridge through the connecting conduit already while it is being filled into the hollow cylinder. The effect of said reverse U-shaped loop of the connecting conduit is that, before the pumping plunger is moved in the direction of the connecting conduit to the cartridge, the monomer liquid in the hollow cylinder remains in the connecting conduit up to the level of the apex, by means of which premature ingress of the monomer liquid towards the cement powder is prevented. In particular in the case of high-viscosity cements, any premature contact, even of very small volumes, of the monomer liquid with the cement powder can lead to clogging of the connecting conduit or of a conduit means provided in the form of a nozzle, as is described in U.S. Pat. No. 8,662,736 B2. The connecting conduit can be transparent or translucent to allow the user to check the monomer transfer by eye. For this purpose, in particular, an inspection window can be provided in the device through which the loop with the highest apex can be seen.

Moreover, the invention can provide the volume in the hollow cylinder to be smaller than or equal to the volume of the monomer liquid in the monomer container.

This prevents air from being pressed along into the cement powder when the pumping plunger is actuated.

Moreover, the invention can provide the internal space of the cartridge to be connected on its lower side to the connecting conduit in liquid-permeable manner.

The connecting conduit can exit into a nozzle in the front face of the internal space in accordance with U.S. Pat. No. 8,662,736 B4. Said nozzle prevents any ingress of cement powder into the connecting means.

In another variant of an embodiment, the internal space of the cartridge is connected on a lateral jacket surface to the connecting conduit in liquid-permeable manner. By this means, it is feasible just as well to transfer the monomer liquid via the side into the cement powder into the internal space of the cartridge.

Preferably, the hollow cylinder, the cartridge, and the connecting conduit as well as, if present, the base, the mixing facility, and the mixing rod consist of a plastic material and can be manufactured inexpensively by plastics injection moulding.

The objects underlying the present invention are also solved by a method for the mixing of a bone cement, in particular by means of a device according to the invention, comprising the chronological steps of:

A) a monomer container is being opened;
B) the monomer liquid flows from the monomer container into a hollow cylinder, whereby the hollow cylinder is bounded on one side by a pumping plunger;
C) the pumping plunger is pushed into the hollow cylinder and thus the monomer liquid is pressed from the hollow cylinder and through a connecting conduit into the internal space of a cartridge, whereby a cement powder is situated in the internal space of the cartridge; and
D) the monomer liquid and the cement powder are being mixed in the internal space of the cartridge.

Preferably, the monomer liquid flows into the hollow cylinder by the action of gravitation.

In this context, the invention can provide the monomer liquid and the cement powder to be mixed in the internal space of the cartridge only once the pumping plunger was pushed into the hollow cylinder either completely or up to a marking, whereby the marking is a measure for the monomer liquid supplied into the internal space of the cartridge.

As a result, it can be insured that the bone cement dough thus produced attains the desired consistency by means of the desired admixture of monomer liquid.

The invention also proposes that the monomer liquid and the cement powder are mixed in the internal space by means of a mixing facility, and that the mixing facility can be operated by moving a mixing rod that is guided into the internal space of the cartridge such that it can be rotated and can be shifted in longitudinal direction, whereby, preferably, the mixing rod is pulled out of the internal space of the cartridge up to the limit stop after the mixing and, particularly preferably, the mixing rod is broken off at a predetermined breakage site after pulling it out up to the limit stop.

As a result, the method can be executed easily by manual operation.

Moreover, the invention can provide the monomer container to be opened by operating or triggering an opening means, whereby it is preferred to have the monomer container be broken open by the opening means.

As a result, the monomer container can be opened inside the device such that the overall device is closed with respect to the outside.

The invention also proposes that the pumping plunger is pushed into the hollow cylinder by means of a tensioned elastic spring element, whereby it is preferred to first release a locking mechanism engaging the pumping plunger and/or the spring element for this purpose.

This attains further optimisation of the method according to the invention and, in addition, prevents possible incorrect operation.

And lastly the invention can provide that the cartridge with the ready-mixed cement dough is released from the connecting conduit, hollow cylinder, and monomer container, and that the ready-mixed cement dough is dispensed from the internal space of the cartridge by advancing a dispensing plunger that is supported such as to be axially mobile in the cartridge and that bounds the internal space of the cartridge on one side.

The invention is based on finding, surprisingly, that a monomer liquid can be pressed from below into the internal space of a cartridge by means of a pumping plunger without any interfering air inclusions concurrently forming in the bone cement. As a result, the device can be used largely without external energy sources or internal energy stores. In particular, there is no need to use vacuum sources and vacuum-type connectors and components, which significantly simplifies the use in less developed places as well as local use or use in field hospitals. Moreover, full-prepacked mixing systems according to the invention are less sensitive to possible disturbances and therefore are very likely to be ready for use since no vacuum leaks can occur.

A device according to the invention and/or a method according to the invention can provide, for example, for the monomer liquid, after a monomer container is being opened, to flow into a hollow cylinder by the action of gravity, to be pressed from the latter into the internal space of the cartridge containing the cement powder by manual actuation of the pumping plunger. This means that the transfer of monomer liquid proceeds by the action of pressure, rather than the action of vacuum, which is in contrast to the mixing systems currently on the market. Said monomer transfer by the action of pressure effected by hand can be realised inexpensively using simple plastic parts that can be produced by plastics injection moulding. The special advantage of the device according to the invention is that the device can be operated in the absence of external aids, such as compressed air-driven vacuum pumps, and in the absence of external energy sources, such as compressed air or electrical current. As a result, the device according to the invention can be used autonomously and can be used even under the simplest operating conditions. The device according to the invention provides a closed full-prepacked mixing system for price-sensitive markets.

It has been evident in the scope of the present invention that the monomer liquid supplied into the cement powder from the underside of the internal space of the cartridge through the action of pressure migrates from bottom to top in a uniform front. By this means, the air that is present in the intervening spaces between the cement powder particles is displaced and pushed out toward the top. As a result, air inclusions are prevented. It has been evident, surprisingly, in the scope of the present invention that a bone cement dough produced by means of a device according to the invention and a method according to the invention is largely free of air inclusions and has a quality that is equal to that of a cement dough produced in a vacuum.

BRIEF DESCRIPTION OF THE DRAWINGS

Further exemplary embodiments of the invention shall be illustrated in the following on the basis of seven schematic figures, though without limiting the scope of the invention. In the figures.

Sectioned surfaces in the cross-sectional views of FIGS. 3, 4, 6, and 7 are identified by hatching.

Figure 1:
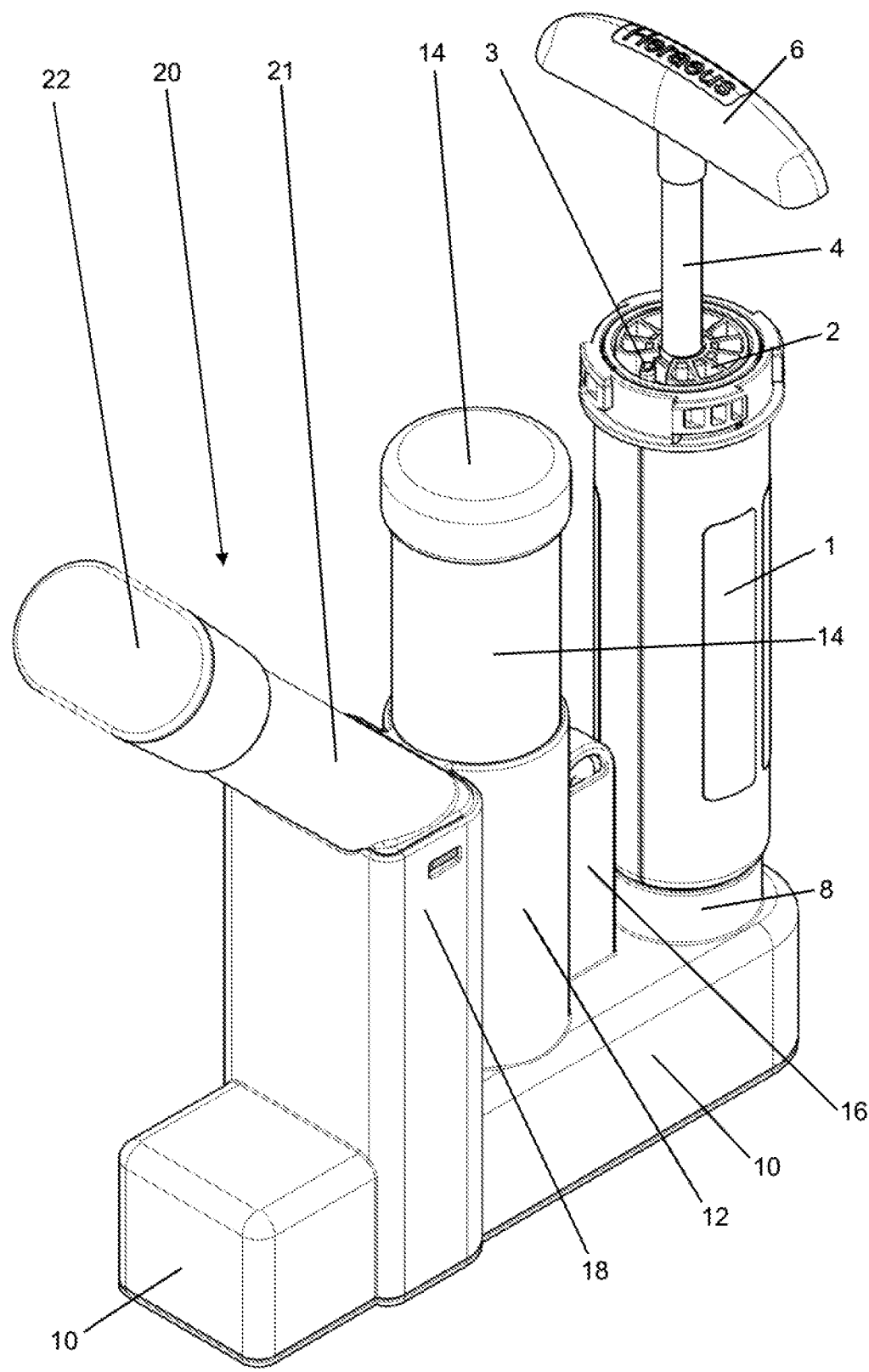
FIG. 1: shows a schematic perspective view of a device according to the invention in the form of a full-prepacked mixing system.
Figure 2:
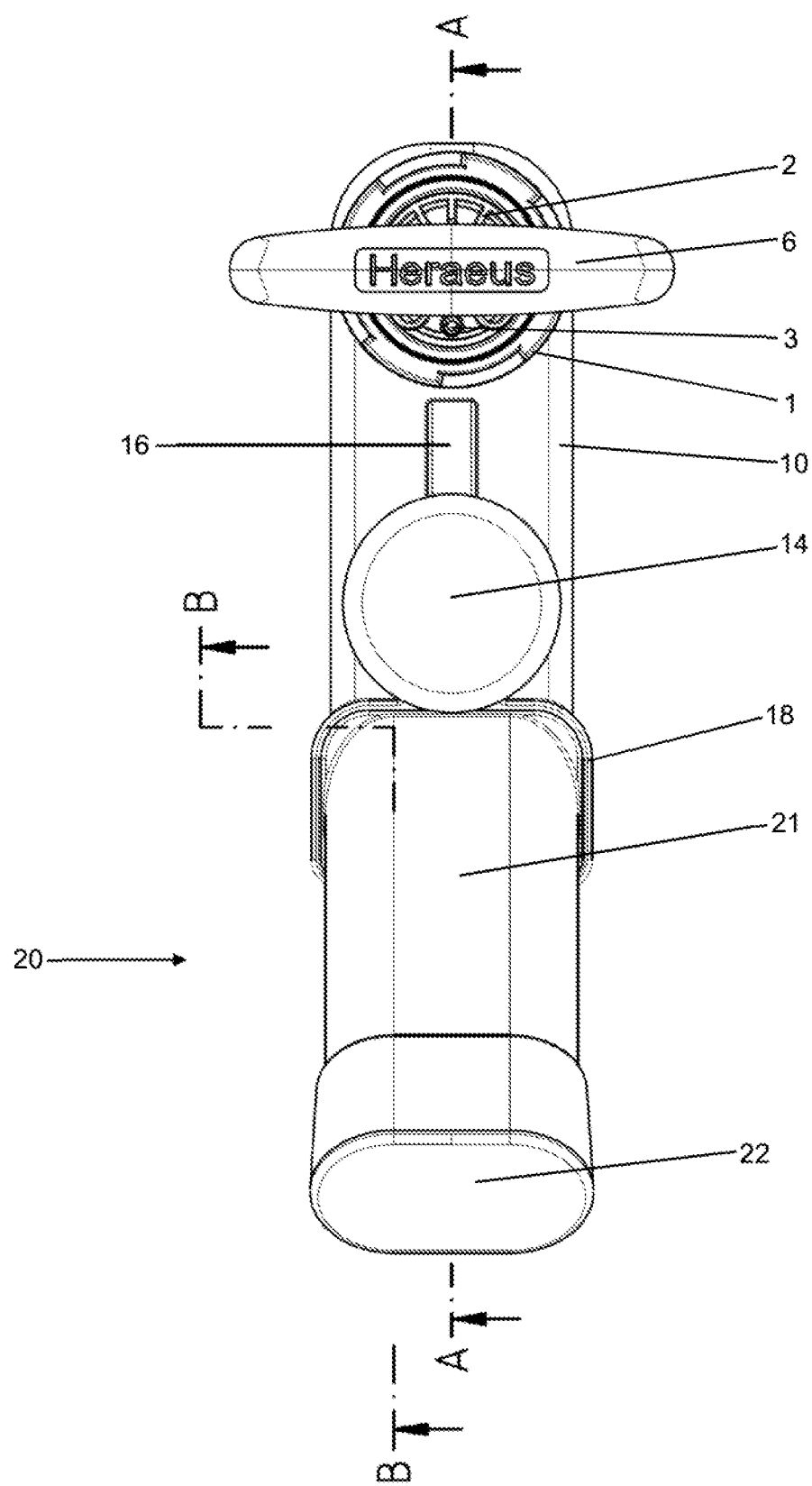
FIG. 2: shows a top view with two sectional planes A and B of the device according to FIG. 1.
Figure 3:
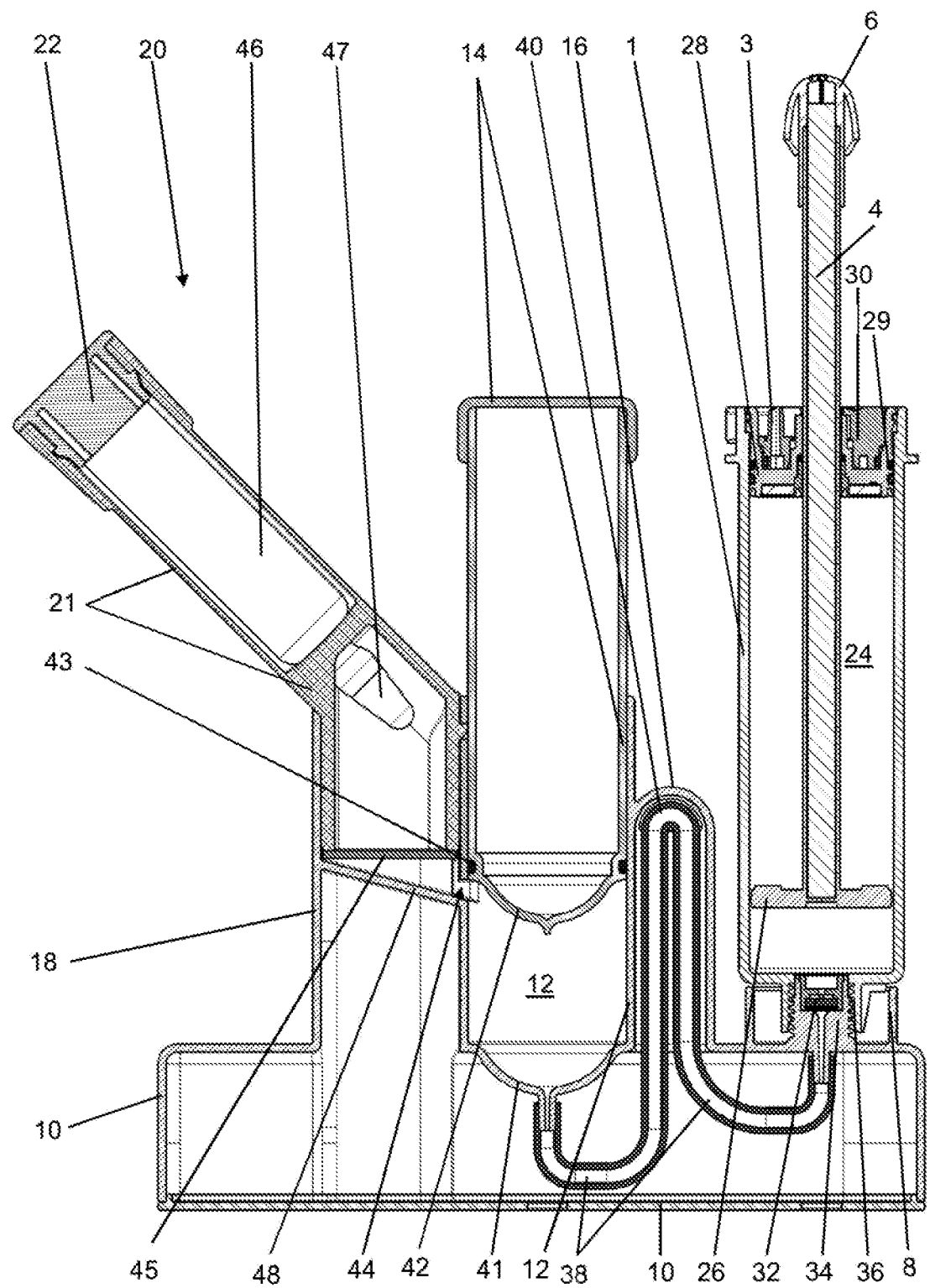
FIG. 3: shows the device according to FIGS. 1 and 2 in a schematic cross-sectional view corresponding to sectional plane A according to FIG. 2.
Figure 4:
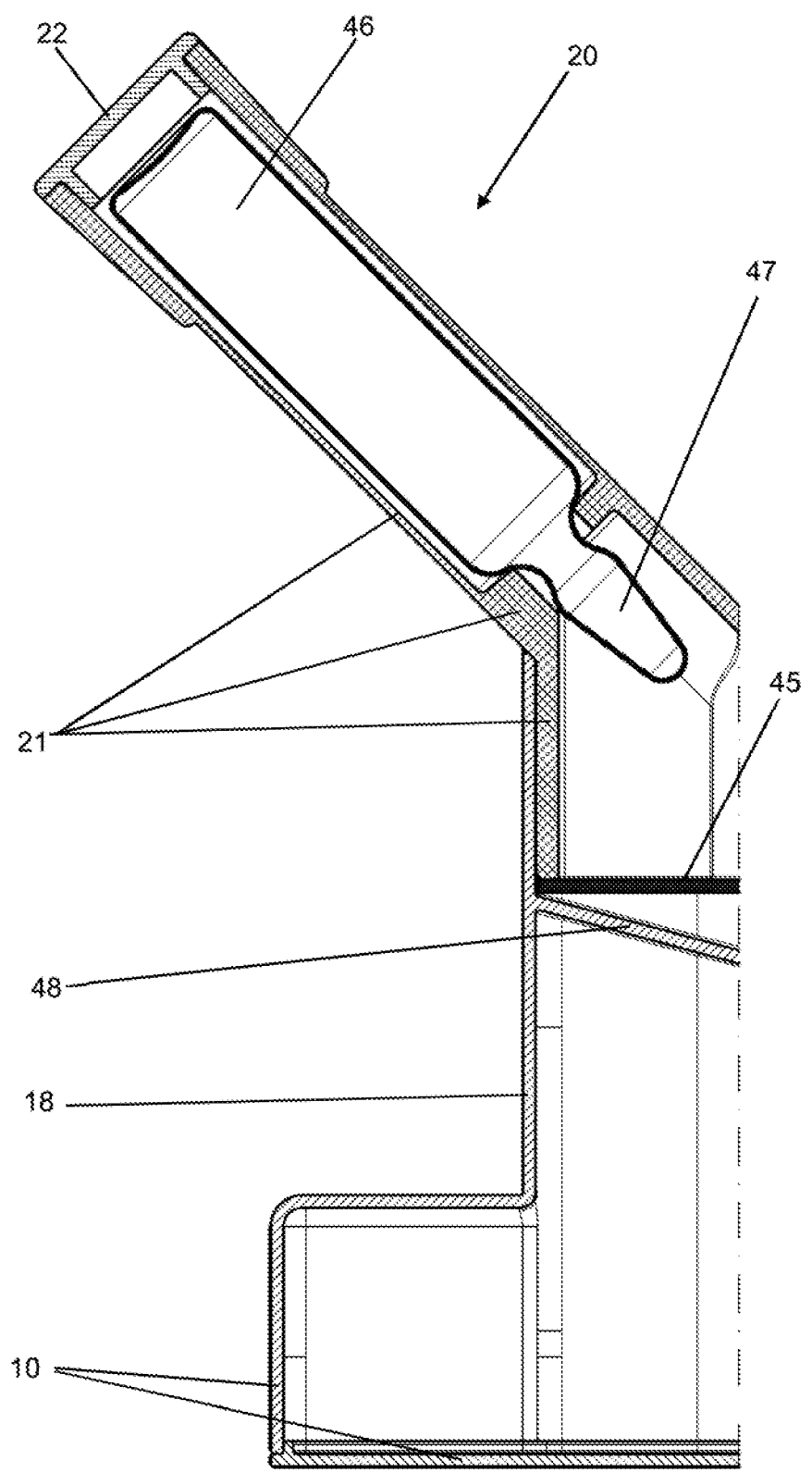
FIG. 4: shows a detail of the device according to FIGS. 1, 2, and 3 in a schematic cross-sectional view corresponding to sectional plane B according to FIG. 2.

FIGS. 1 to 4 shows schematically views of a first device according to the invention that is well-suited for executing a method according to the invention. In this context, FIG. 1 shows a schematic perspective view of a device according to the invention in the form of a full-prepacked mixing system, FIG. 2 shows a top view with two sectional planes A and B of the device according to FIG. 1, FIG. 3 shows the device according to FIGS. 1 and 2 in a schematic cross-sectional view corresponding to sectional plane A according to FIG. 2, and FIG. 4 shows a detail of said device according to FIGS. 1, 2, and 3 in a schematic cross-sectional view corresponding to sectional plane B according to FIG. 2.

The device comprises a cartridge 1 that contains a cement powder as starting component of the PMMA bone cement to be produced. The cartridge 1 is closed on the top side (on the top in FIGS. 1 and 3, in the direction of the observer in FIG. 2) by means of a dispensing plunger 2. The dispensing plunger 2 can be locked with respect to the walls of the cartridge 1. A vacuum connector 3 is provided in the dispensing plunger 2 and can be used to evacuate the inside of the cartridge 1 and, theoretically, ethylene oxide can be filled in through the vacuum connector 3 for sterilisation of the content of the cartridge 1. A mixing rod 4 is guided through a centric feed-through in the dispensing plunger 2 and can be pulled in and out of the cartridge 1 and is supported like in a bearing such that it can rotate in the dispensing plunger 2 and thus in the cartridge 1. A handle part 6 for manual operation of the mixing rod 4 is attached on the upper end of the mixing rod 4 (on the top in FIGS. 1 and 3, in the direction of the observer in FIG. 2).

The cartridge 1 is attached to the base 10 in releasable manner in the area of a socket 8 on the base 10 of the device. Provided to be the same part as base 10, a hollow cylinder 12 is arranged on the upper side of the base 10 and has a pumping plunger 14 arranged in it, which fits inside it and can be pressed and/or pushed into the inside of the hollow cylinder 12 (downwards in FIGS. 1 and 3, into the image plane from the direction of the observer in FIG. 2).

Aside from the hollow cylinder 12, there is a connecting socket 18 provided on the base 10 and forms a part of a connector 20 for a monomer container 46 of the device. Aside from the connecting socket 18, the connector 20 for the monomer container 46 comprises an elastic receptacle 21 for the monomer container 46 and a lid 22 by means of which the connector 20 for the monomer container 46 can be closed with respect to the outside after the monomer container 46 was inserted. The monomer container 46 is arranged on the inside of the connector 20 and in the device. The monomer container 46 is a glass ampoule filled with a monomer liquid as second component for the PMMA bone cements to be produced. The elastic receptacle 21 consists of rubber or another elastic plastic material.

Further details on the design of the device are evident from FIGS. 3 and 4. The inside of the cartridge 1 is formed by a cylindrical internal space 24 that contains the cement powder. Moreover, the internal space 24 of the cartridge 1 has a mixing facility 26 consisting of multiple mixing vanes 26 arranged in it that is attached to the mixing rod 4 and can be moved in the internal space 24 by means of the mixing rod 4. The dispensing plunger 2 is designed to be two-part and consists of a sterilisation plunger 28 (upper part of the dispensing plunger in FIG. 3) and a sealing plunger 30 (lower part of the dispensing plunger in FIG. 3) that is sealed with respect to the internal wall of the internal space 24 by means of a seal 29. The sealing plunger 30 comprises a gas-permeable, but powder-impermeable pore disk through which the internal space 24 can be evacuated. The dispensing plunger 2 has a cylindrical external circumference and closes tight against the walls of the internal space 24. The dispensing plunger 2 can be propelled in the internal space 24 in the direction of a dispensing opening that is arranged on the side of the internal space 24 of the cartridge 1 that is opposite from the dispensing plunger 2.

For connection of the cartridge 1 to the base 10, a base connector 34 that has an external thread and has a powder-impermeable and liquid-permeable filter 32 arranged in it is provided as connection to the cartridge 1. A cartridge connector 36 having an internal thread matching the external thread of the base connector 34 is provided on the side of the internal space 24 of the cartridge 1 that is opposite from the dispensing plunger 2. The cartridge connector 36 bounds the dispensing opening of the cartridge 1. The cartridge connector 36 is screwed onto and closes tight against the base connector 34.

A connecting conduit 34 is provided between the hollow cylinder 12 and the internal space 24 of the cartridge 1 and connects the hollow cylinder 12 to the internal space 24 of the cartridge 1. The filter 32 that prevents cement powder from entering from the internal space 24 of the cartridge 1 into the connecting conduit 38 is arranged on the junction into the internal space 24 of the cartridge 1. The connecting conduit 38 forms a loop 40 that has a high apex in order to prevent any uncontrolled passage of monomer liquid through the connecting conduit 38 into the internal space 24 of the cartridge 1. A housing 16 having a small inspection window is provided for covering and visual inspection of the loop 40.

The socket 8, base 10, hollow cylinder 12, housing 16, and connecting socket 18 for the monomer container 46 are produced in the form of a single part from a plastic material, for example by injection moulding. The hollow cylinder 12 is limited on its underside (on the bottom in FIG. 3) by means of a funnel-shaped floor 41 that tapers steadily in downward direction. This ensures that all of the monomer liquid can flow and/or be pushed from the hollow cylinder 12. The pumping plunger 14 is formed by a hollow body made of a plastic material and is shaped, on its bottom surface 42, as a negative image of the floor 41 of the hollow cylinder 12. The pumping plunger 14 is sealed with respect to the internal wall of the hollow cylinder 12 by means of a seal 43 and is supported as in a bearing in the hollow cylinder 12 such that it is mobile in longitudinal direction (downwards in FIG. 3).

A junction 44 of the connector 20 for the monomer container 46 into the hollow cylinder 12 is provided on a jacket surface of the hollow cylinder 12, right below the lower surface 42 of the pumping plunger 14. The junction 44 forms a conduit means for the monomer liquid such that the junction 44 can be interpreted to be part of a connecting conduit 38, 44 for the monomer liquid that has the hollow cylinder 12 arranged in it.

A sieve 45 or filter 45 by means of which fragments and parts of the opened monomer container 46 can be trapped is arranged in the connector 20 for the monomer container 46. The monomer container 46 is a glass ampoule 46 that has an ampoule head 47 that can be broken off and a neck that can be broken open, whereby the neck connects the ampoule head 47 to the body of the ampoule 46. Due to the elasticity of the receptacle 21 for the monomer container 46 and due to the receptacle 21 being broadened in the area of the neck, bending the receptacle 21 with the monomer container 46 in it allows the head 47 of the monomer container 46 to be broken off. By this means, the receptacle 21 having appropriate shape, in particular being broadened in the area of the neck, forms an opening means 21 for opening of the monomer container 46. Other opening means for shearing off the head 47 of the monomer container 46 can be implemented just as well.

An inclined floor surface 48 that is inclined in the direction of the junction 44 is provided in the connecting socket 18 below the sieve 45 and/or filter 45. By this means, the entire monomer liquid can flow from the monomer container 46 through the junction 44 into the hollow cylinder 12.

A method according to the invention can be implemented by means of the device according to FIGS. 1 to 4, for example as follows. The device is placed, by the base 10, on a table or any other fitting level support. The monomer container 46 is opened by kinking the elastic receptacle 21 by breaking off and/or breaking open the head 47. The monomer liquid from the monomer container 46 flows through the sieve 45 and/or the filter 45, whereby fragments of the monomer container 46 are retained. The inclined floor surface 48 guides the monomer liquid through the junction 44 into the hollow cylinder 12. The unoccupied internal space of the hollow cylinder 12 is getting filled completely with the monomer liquid, since the monomer container 46 contains more monomer liquid than can be taken up by the hollow cylinder 12. Air inclusions escape through the junction 44, since the junction 44 is situated at the topmost place of the space bounded by the hollow cylinder 12 and the pumping plunger 14. In this context, the monomer liquid cannot flow beyond the apex of the loop 40 since the loop 40 is arranged clearly above the junction 44 and also is arranged above the liquid level of the monomer liquid in the connector 20 such that the monomer liquid will not rise to this level in the absence of pressure.

Subsequently, the pumping plunger 14 can be pushed completely or partly into the hollow cylinder 12 in order to transfer and/or press the desired amount of monomer liquid from the hollow cylinder 12 through the connecting conduit 38 into the internal space 24 of the cartridge 1. The amount of monomer liquid that is pressed in can be adjusted by inserting the pumping plunger 14 into the hollow cylinder 12 to different depth levels. For this purpose, markings (not shown) can be provided on the outside of the pumping plunger 14 or markings are situated on the hollow cylinder 12 and the hollow cylinder 12 consists of a transparent material. The monomer liquid is being pressed through the filter 32 into the internal space 24 of the cartridge 1 and there it rises and mixes with the cement powder that is stored in the internal space 24 of the cartridge 1.

After the desired amount was filled into the internal space 24 of the cartridge 1, the mixing facility 26 and/or the mixing rod 4 is/are pushed in, pulled out, and rotated by means of the handle part 6 to manually mix the monomer liquid and the cement powder, and the cement dough and/or the PMMA bone cement is thus being mixed. After the mixing is completed, the mixing rod 4 is pulled out of the internal space 24 of the cartridge 1 up to the limit stop and is broken off to make sure that it does not interfere at a later point in time. If applicable, a locking mechanism of the dispensing plunger 2 can be released. Subsequently, the cartridge 1 is unscrewed from the base 10 and a dispensing tube (not shown) can be screwed onto the internal thread on the cartridge connector 36. Subsequently, the ready-mixed bone cement can be expelled from the internal space of the cartridge through the dispensing opening and the dispensing tube by pressing the dispensing plunger 2 inwards, and the ready-mixed bone cement can be applied.

Figure 5:
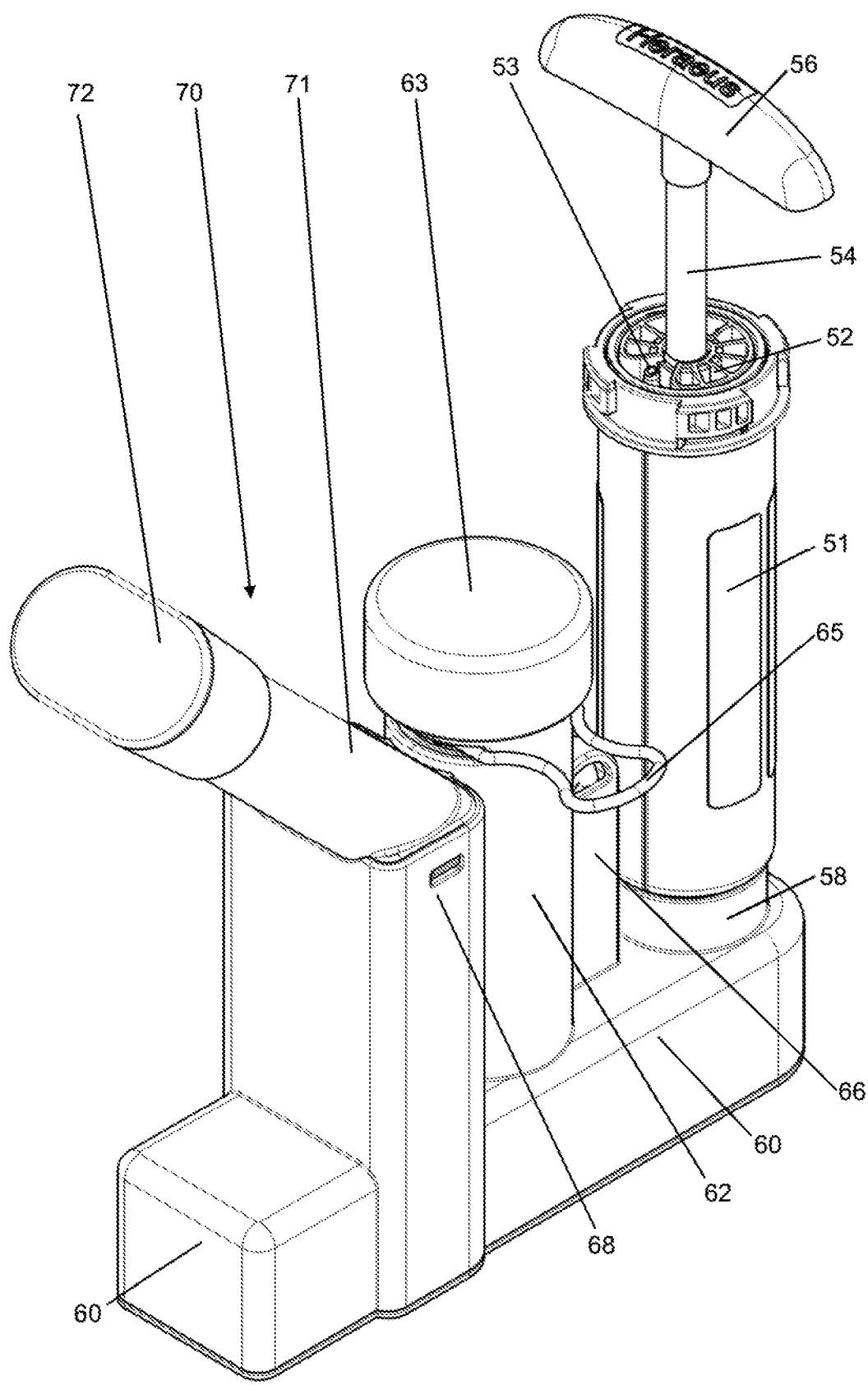
FIG. 5: shows a schematic perspective view of an alternative device according to the invention in the form of a full-prepacked mixing system.
Figure 6:
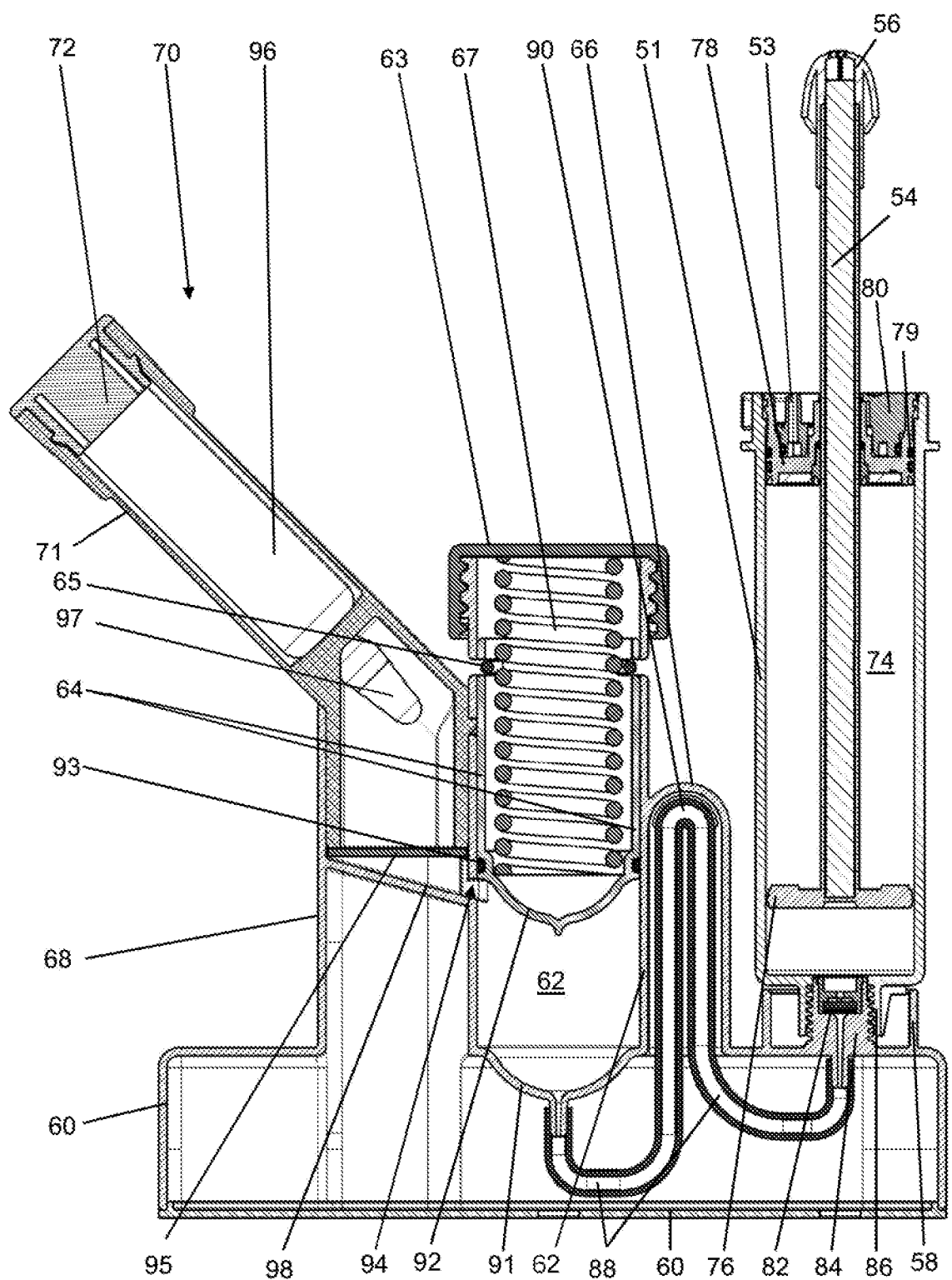
FIG. 6: shows the device according to FIG. 5 in a schematic cross-sectional view.
Figure 7:
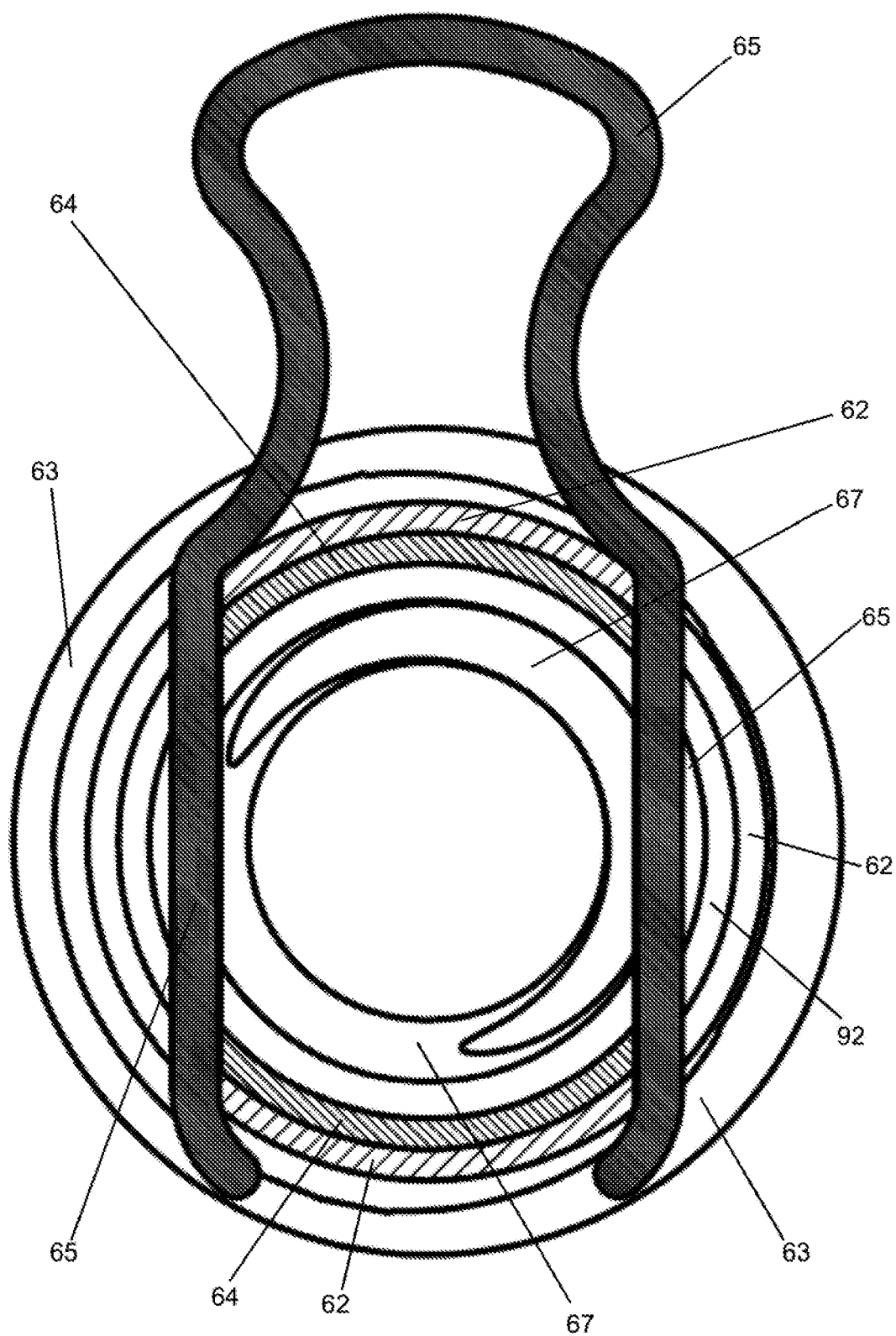
FIG. 7: shows a schematic cross-sectional view of a detail of the device according to FIGS. 4 and 5, namely of the hollow cylinder with a clasp as locking mechanism for a compression spring.

FIGS. 5 to 7 shows schematic views of a second, alternative device according to the invention that is well-suited for executing a method according to the invention. In this context, FIG. 5 shows a schematic perspective view of an alternative device according to the invention in the form of a full-prepacked mixing system, FIG. 6 shows the device according to FIG. 5 in a schematic cross-sectional view, and FIG. 7 shows a schematic cross-sectional view of a detail of the device according to FIGS. 4 and 5.

The device comprises a cartridge 51 that contains a cement powder as starting component of the PMMA bone cement to be produced. The cartridge 51 is closed on the top side (towards the top in FIGS. 5 and 6) by means of the dispensing plunger 52. The dispensing plunger 52 can be locked with respect to the walls of the cartridge 51. A vacuum connector 53 is provided in the dispensing plunger 52 and can be used to evacuate the inside of the cartridge 51 and, theoretically, ethylene oxide can be filled in through the vacuum connector 3 for sterilisation of the content of the cartridge 51. A mixing rod 54 is guided through a centric feed-through in the dispensing plunger 52 and can be pulled in and out of the cartridge 51 and is supported like in a bearing such that it can rotate in the dispensing plunger 52 and thus in the cartridge 51. A handle part 56 for manual operation of the mixing rod 4 is attached on the upper end of the mixing rod 54 (on the top in FIGS. 5 and 6).

The cartridge 51 is attached to the base 60 in releasable manner in the area of a socket 58 on the base 60 of the device. A hollow cylinder 62 that is closed by means of a screw lid 63 is provided as the same part as the base 60 and is arranged on the top side of the base 60. A fitting pumping plunger 64 that can be pressed and/or pushed into the inside of the hollow cylinder 62 (downwards in FIGS. 5 and 6) is arranged in the hollow cylinder 62. The pumping plunger 64 is locked by means of a clasp 65 acting as locking mechanism 65 such that it cannot be moved into the inside of the hollow cylinder 62 without releasing the clasp 65 and/or the locking mechanism 65. A tensioned compression spring 67 that rests against the screw lid 63 is arranged on the inside of the pumping plunger 64. After the clasp 65 and/or the locking mechanism 65 is released by pulling it out (pulling upwards in FIG. 7), the compression spring 67 pushes the pumping plunger 64 downwards into the hollow cylinder 62.

Aside from the hollow cylinder 62, there is a connecting socket 68 provided on the base 60 and forms a part of a connector 70 for a monomer container 96 of the device. Aside from the connecting socket 68, the connector 70 for the monomer container 96 comprises an elastic receptacle 71 for the monomer container 96 and a lid 72 by means of which the connector 70 for the monomer container 96 can be closed with respect to the outside after the monomer container 96 was inserted. The monomer container 96 is arranged on the inside of the connector 70 and in the device. The monomer container 96 is a glass ampoule filled with a monomer liquid as second component for the PMMA bone cements to be produced. The elastic receptacle 71 consists of rubber or another elastic plastic material.

Further details on the design of the device are evident from FIGS. 6 and 7. The inside of the cartridge 51 is formed by a cylindrical internal space 74 that contains the cement powder. Moreover, the internal space 74 of the cartridge 51 has a mixing facility 76 consisting of multiple mixing vanes 76 arranged in it that is attached to the mixing rod 54 and can be moved in the internal space 74 by means of the mixing rod 54. The dispensing plunger 52 is designed to be two-part and consists of a sterilisation plunger 78 (upper part of the dispensing plunger in FIG. 6) and a sealing plunger 80 (lower part of the dispensing plunger in FIG. 6) that is sealed with respect to the internal wall of the internal space 74 by means of a seal 79. The sealing plunger 80 comprises a gas-permeable, but powder-impermeable pore disk through which the internal space 74 can be evacuated. The dispensing plunger 52 has a cylindrical external circumference and closes tight against the walls of the internal space 74. The dispensing plunger 52 can be propelled in the internal space 74 in the direction of a dispensing opening that is arranged on the side of the internal space 74 of the cartridge 51 that is opposite from the dispensing plunger 52.

For connection of the cartridge 51 to the base 60, a base connector 84 that has an external thread and has a powder-impermeable and liquid-permeable filter 82 arranged in it is provided as connection to the cartridge 1. A cartridge connector 86 having an internal thread matching the external thread of the base connector 84 is provided on the side of the internal space 74 of the cartridge 51 that is opposite from the dispensing plunger 52. The cartridge connector 86 bounds the dispensing opening of the cartridge 51. The cartridge connector 86 is screwed onto and closes tight against the base connector 84.

A connecting conduit 88 is provided between the hollow cylinder 62 and the internal space 74 of the cartridge 51 and connects the hollow cylinder 62 to the internal space 74 of the cartridge 51. The filter 82 that prevents cement powder from entering from the internal space 74 of the cartridge 51 into the connecting conduit 88 is arranged on the junction into the internal space 74 of the cartridge 51. The connecting conduit 88 forms a loop 90 that has a high apex in order to prevent any uncontrolled passage of monomer liquid through the connecting conduit 88 into the internal space 74 of the cartridge 51. A housing 66 having a small inspection window is provided for covering and visual inspection of the loop 80.

The socket 58, base 60, hollow cylinder 62, housing 66, and connecting socket 68 for the monomer container 96 are produced in the form of a single part from a plastic material, for example by injection moulding. The hollow cylinder 62 is limited on its underside (on the bottom in FIG. 6) by means of a funnel-shaped floor 91 that tapers steadily in downward direction. This ensures that all of the monomer liquid can flow and/or be pushed from the hollow cylinder 62. The pumping plunger 64 is formed by a hollow body made of a plastic material and is shaped, on its bottom surface 92, as a negative image of the floor 91 of the hollow cylinder 62. The pumping plunger 64 is sealed with respect to the internal wall of the hollow cylinder 62 by means of a seal 93 and is supported as in a bearing in the hollow cylinder 62 such that it is mobile in longitudinal direction (downwards in FIG. 6).

A junction 94 of the connector 70 for the monomer container 96 into the hollow cylinder 62 is provided on a jacket surface of the hollow cylinder 62, right below the lower surface 92 of the pumping plunger 64. The junction 94 forms a conduit means for the monomer liquid such that the junction 94 can be interpreted to be part of a connecting conduit 88, 94 for the monomer liquid that has the hollow cylinder 62 arranged in it.

A sieve 95 or filter 95 by means of which fragments and parts of the opened monomer container 96 can be trapped is arranged in the connector 70 for the monomer container 96. The monomer container 96 is a glass ampoule 96 that has an ampoule head 97 that can be broken off and a neck that can be broken open, whereby the neck connects the ampoule head 97 to the body of the ampoule 96. Due to the elasticity of the receptacle 71 for the monomer container 96 and due to the receptacle 71 being broadened in the area of the neck, bending the receptacle 71 with the monomer container 96 in it allows the head 97 of the monomer container 96 to be broken off. By this means, the receptacle 71 having appropriate shape, in particular being broadened in the area of the neck, forms an opening means 71 for opening of the monomer container 96. Other opening means for shearing off the head 97 of the monomer container 96 can be implemented just as well.

An inclined floor surface 98 that is inclined in the direction of the junction 94 is provided in the connecting socket 68 below the sieve 95 and/or filter 95. By this means, the entire monomer liquid can flow from the monomer container 96 through the junction 94 into the hollow cylinder 62.

A method according to the invention can be implemented by means of the device according to FIGS. 5 to 7, for example as follows. The device is placed, by the base 60, on a table or any other fitting level support. The monomer container 96 is opened by kinking the elastic receptacle 71 by breaking off and/or breaking open the head 97. The monomer liquid from the monomer container 96 flows through the sieve 95 and/or the filter 95, whereby fragments of the monomer container 96 are retained. The inclined floor surface 98 guides the monomer liquid through the junction 94 into the hollow cylinder 62. The unoccupied internal space of the hollow cylinder 62 is getting filled completely with the monomer liquid, since the monomer container 96 contains more monomer liquid than can be taken up by the hollow cylinder 62. Air inclusions escape through the junction 94, since the junction 44 is situated at the topmost place of the space bounded by the hollow cylinder 62 and the pumping plunger 64. In this context, the monomer liquid cannot flow beyond the apex of the loop 90 since the loop 40 is arranged clearly above the junction 94 and also is arranged above the liquid level of the monomer liquid in the connector 70 such that the monomer liquid will not rise to this level in the absence of pressure.

Subsequently, the clasp 65 is pulled out of the device and, thus, the pumping plunger is unlocked. Due to the mechanical tension of the compression spring 67, the pumping plunger 64 is then pushed fully into the hollow cylinder 62 and by this means the monomer liquid is transferred and/or pressed from the hollow cylinder 62 through the connecting conduit 88 into the internal space 74 of the cartridge 51. The monomer liquid is being pressed through the filter 82 into the internal space 74 of the cartridge 51 and there it rises and mixes with the cement powder that is stored in the internal space 74 of the cartridge 51.

After the monomer liquid was filled into the internal space 74 of the cartridge 51, the mixing facility 76 and/or the mixing rod 54 is/are pushed in, pulled out, and rotated by means of the handle part 56 to manually mix the monomer liquid and the cement powder, and the cement dough and/or the PMMA bone cement is thus being mixed. After the mixing is completed, the mixing rod 54 is pulled out of the internal space 74 of the cartridge 51 up to the limit stop and is broken off to make sure that it does not interfere at a later point in time. If applicable, a locking mechanism of the dispensing plunger 52 can be released. Subsequently, the cartridge 51 is unscrewed from the base 60 and a dispensing tube (not shown) can be screwed onto the internal thread on the cartridge connector 86. Subsequently, the ready-mixed bone cement can be expelled from the internal space of the cartridge through the dispensing opening and the dispensing tube by pressing the dispensing plunger 52 inwards, and the ready-mixed bone cement can be applied.

The features of the invention disclosed in the preceding description and in the claims, figures, and exemplary embodiments, can be essential for the implementation of the various embodiments of the invention both alone and in any combination.

LIST OF REFERENCE NUMBERS 1, 51 Cartridge
2, 52 Dispensing plunger
3, 53 Vacuum connector
4, 54 Mixing rod
6, 56 Handle part
8, 58 Socket
10, 60 Base
12, 62 Hollow cylinder
14, 64 Pumping plunger
16, 66 Housing for loop of the connecting conduit
18, 68 Connector socket
20, 70 Connector for the monomer container
21, 71 Elastic receptacle for the monomer container/opening means
22, 72 Lid
24, 74 Internal space of the cartridge
26, 76 Mixing vanes/mixing facility
28, 78 Sterilisation plunger
29, 79 Seal
30, 80 Sealing plunger
32, 82 Powder-impermeable and liquid-permeable filter
34, 84 Base connector with external thread
36, 86 Cartridge connector with internal thread
38, 88 Connecting conduit
40, 90 Loop of the connecting conduit
41, 91 Floor of the hollow cylinder
42, 92 Lower surface of the pumping plunger
43, 93 Seal
44, 94 Junction into the hollow cylinder/connecting conduit
45, 95 Sieve/filter
46, 96 Glass ampoule/monomer container
47, 97 Head of the glass ampoule/head of the monomer container
48, 98 Inclined floor surface of the connector for the monomer container
63 Screw lid
65 Locking mechanism/clasp
67 Tensioned compression spring

The invention claimed is:

1. A device for the mixing of polymethylmethacrylate bone cement and for storing monomer liquid and cement powder as starting components of the bone cement, the device comprising:

a cartridge (1, 51) having an internal space (24, 74) for mixing the bone cement, which is closed on one side by a mobile dispensing plunger (2, 52);

a connector (20, 70) configured for attachment of a monomer container (46, 96) for monomer liquid, such that, when attached, the monomer container (46, 96) is openable appropriately in the device and the monomer liquid is flowable from an opened monomer container (46, 96) into a hollow cylinder (12, 62) of the device, and a connecting conduit (38, 88) through which the monomer liquid can be guided into the internal space (24, 74) of the cartridge (1, 51), wherein the hollow cylinder (12, 62) is connected to the connecting conduit (38, 88) and the hollow cylinder (12, 62) is arranged between the connector and the internal space (24, 74) of the cartridge (1, 51), a pumping plunger (14, 64) that can be shifted axially in the hollow cylinder (12, 62) is arranged in the hollow cylinder (12, 62), the connecting conduit (38, 88) connects the hollow cylinder (12, 62) to the internal space (24, 74) of the cartridge (1, 51), and the connector (20, 70) terminates into the hollow cylinder (12, 62) on a jacket surface of the hollow cylinder such that the monomer liquid is flowable into the hollow cylinder, the pumping plunger (14, 64) is actuatable to push monomer liquid from the hollow cylinder (12, 62) through the connecting conduit (38, 88) into the internal space (24, 74) of the cartridge (1, 51), and the monomer liquid and cement powder are mixable in the internal space (24, 74) of the cartridge (1, 51).

2. The device according to claim 1, wherein a mixing facility (26, 76) that can be operated from outside the device, is arranged in the cartridge (1, 51), whereby the mixing facility (26, 76) optionally can be operated by means of a mixing rod (4, 54) that is guided through a feed-through in the dispensing plunger (2, 52) into the inside of the cartridge (1, 51) and is supported as in a bearing such as to be mobile.

3. The device according to claim 1, wherein the dispensing plunger (2, 52) is impermeable for powder, whereby it is optional to have a pore filter that is permeable for gas and impermeable for powder arranged in the dispensing plunger (2, 52).

4. The device according to claim 1, wherein the internal space (24, 74) of the cartridge (1, 51) contains the cement powder.

5. The device according to claim 1, wherein a filter (32, 82) that is impermeable for the cement powder and permeable for the monomer liquid is arranged between the connecting conduit (38, 88) and the internal space (24, 74) of the cartridge (1, 51).

6. The device according to claim 1, wherein the device comprises a base (10, 60), in which at least a part of the connecting conduit (38, 88) is arranged, whereby the cartridge (1, 51) is connected to the base (10, 60) in detachable manner, optionally by means of a screw thread, whereby a cement powder-impermeable and monomer liquid-permeable filter (32, 82) optionally is arranged in the base (10, 60) of the device, optionally in the connection (34,84) to the cartridge (1, 51) of the base (10, 60).

7. The device according to claim 6, wherein the hollow cylinder (12, 62) or the hollow cylinder (12, 62) and the connector (20, 70) are connected to the base (10, 60), optionally in non-releasable manner.

8. The device according to claim 1, wherein the connector (20, 70) terminates into the hollow cylinder (12, 62) right below the pumping plunger (14, 64).

9. The device according to claim 1, wherein the device comprises an opening means (21, 71) for opening an attachable monomer container (46, 96) by means of which the attachable monomer container (46, 96) is openable inside the device, whereby it is optional to have a sieve (45, 95) or a filter (45, 95) arranged in the connection from the connector (20, 70) to the hollow cylinder (12, 62) by means of which fragments or shreds of the opened monomer container (46, 96) can be retained.

10. The device according to claim 1, wherein an attachable monomer container (46, 96) is arranged above the connection from the hollow cylinder (12, 62).

11. The device according to claim 1, wherein the connecting conduit (38, 44, 88, 94) is connected to the hollow cylinder (12, 62) on a lower side.

12. The device according to claim 1, wherein the hollow cylinder (12, 62) comprises, on a side opposite from the pumping plunger (14, 64), a floor (41, 91) that is conical, semi-spherical or tapering downwards in any other way, whereby the surface (42, 92) of the pumping plunger (14, 64) facing the floor (41, 91) of the hollow cylinder (12, 62) forms a negative image of the floor (41, 91).

13. The device according to claim 1, wherein the pumping plunger (14, 64) can be moved axially in the hollow cylinder (12, 62) by hand.

14. The device according to claim 1, wherein the hollow cylinder (12, 62) is transparent and comprise markings indicating the fill level of a liquid in the hollow cylinder (12, 62).

15. The device according to claim 1, wherein the hollow cylinder (12, 62) comprises an internal thread and the pumping plunger (14, 64) comprises a matching external thread such that the pumping plunger (14, 64) can be screwed into the hollow cylinder (12, 62) in order to press the monomer liquid from the hollow cylinder (12, 62) into the internal space (24, 74) of the cartridge (1, 51).

16. The device according to claim 1, wherein the device comprises a tensioned compression spring (67) and a locking mechanism (65), whereby the compression spring (67) and/or the pumping plunger (64) is or are locked by the locking mechanism (65) in releasable manner, whereby the compression spring (67), when the locking mechanism (65) is released, exerts a pressure on the pumping plunger (64) to the effect that the pumping plunger (64) is pressed into the hollow cylinder (62).

17. The device according to claim 1, wherein the dispensing plunger (2, 52) is connected to the cartridge (1, 51) by means of a releasable snap-in device, whereby the snap-in device can be released manually by the action of an axial force, such that the dispensing plunger (2, 52) can be moved axially in the internal space (24, 74) of the cartridge (1, 51).

18. The device according to claim 1, wherein the connecting conduit (38, 44, 88, 94) between the hollow cylinder (12, 62) and the internal space (24, 74) of the cartridge (1, 51) comprises a loop (40, 90) that points upwards, whereby the topmost point of the loop (40, 90) is situated above a junction (44, 94) of the connector (20, 70) into the hollow cylinder (12, 62).

19. The device according to claim 1, wherein the volume in the hollow cylinder (12, 62) is smaller than or equal to the volume of the monomer liquid in an attachable monomer container (46, 96).

20. The device according to claim 1, wherein the internal space (24, 74) of the cartridge (1, 51) is connected, on a lower side of the internal space (24, 74), to the connecting conduit (38, 88) in liquid-permeable manner.

21. A method for the mixing of a bone cement comprising the chronological steps of:
A) providing a device comprising
a cartridge (1, 51) having an internal space (24, 74) for mixing the bone cement, which is closed on one side by a mobile dispensing plunger (2, 52);
a monomer container (46,96) containing a monomer liquid;
a connector (20, 70) for attachment of the monomer container (46, 96), such that the monomer container (46, 96) is openable appropriately in the device such that the monomer liquid flows from the opened monomer container (46, 96) into a hollow cylinder (12, 62) of the device; and
a connecting conduit (38, 88) through which the monomer liquid can be guided into the internal space (24, 74) of the cartridge (1, 51),
wherein the hollow cylinder (12, 62) is connected to the connecting conduit (38, 88) and the hollow cylinder (12, 62) is arranged between the connector for the monomer container (46, 96) and the internal space (24, 74) of the cartridge (1, 51), wherein a pumping plunger (14, 64) that can be shifted axially in the hollow cylinder (12, 62) is arranged in the hollow cylinder (12, 62), wherein the connecting conduit (38, 88) connects the hollow cylinder (12, 62) to the internal space (24, 74) of the cartridge (1, 51), such that the pumping plunger (14, 64) can be used to push monomer liquid from the hollow cylinder (12, 62) through the connecting conduit (38, 88) into the internal space (24, 74) of the cartridge (1, 51) by actuating the pumping plunger (14, 64), wherein the connector (20,70) for attachment of the monomer container (46, 96) terminates into the hollow cylinder (12, 62) on a jacket surface of the hollow cylinder (12, 62);
B) opening the monomer container (46, 96);
C) flowing the monomer liquid from the monomer container (46, 96) into the hollow cylinder (12, 62), wherein the hollow cylinder (12, 62) is bounded on one side by the pumping plunger (14, 64);
D) pushing the pumping plunger (14, 64) into the hollow cylinder (12, 62) and thus pressing the monomer liquid from the hollow cylinder (12, 62) and through the connecting conduit (38, 88) into the internal space (24, 74) of the cartridge (1, 51), wherein a cement powder is situated in the internal space (24, 74) of the cartridge (1, 51); and
E) mixing the monomer liquid and the cement powder in the internal space (24, 74) of the cartridge (1, 51).

22. The method according to claim 21, wherein
the monomer liquid and the cement powder are mixed in the internal space (24, 74) of the cartridge (1, 51) only once the pumping plunger (14, 64) is pushed into the hollow cylinder (12, 62) either completely or up to a marking, whereby the marking is a measure for the monomer liquid supplied into the internal space (24, 74) of the cartridge (1, 51).

23. The method according to claim 21, wherein
the monomer liquid and the cement powder are mixed in the internal space (24, 74) by means of a mixing facility (26, 76), by operating the mixing facility (26, 76) by moving a mixing rod (4, 54) that is guided into the internal space (24, 74) of the cartridge (1, 51) such that it can be rotated and can be shifted in longitudinal direction, whereby the mixing rod (4, 54) is pulled out of the internal space (24, 74) of the cartridge (1, 51) up to the limit stop after the mixing and, optionally, the mixing rod (4, 54) is broken off at a predetermined breakage site after pulling it out up to the limit stop.

24. The method according to claim 21, wherein
the monomer container (46, 96) is opened by operating or triggering an opening means (21, 71), whereby it is optional to have the monomer container (46, 96) broken open by the opening means (21, 71).

25. The method according to claim 21, wherein
the pumping plunger (14, 64) is pushed into the hollow cylinder (12, 62) by means of a tensioned elastic spring element (67), whereby it is optional to first release a locking mechanism (65) engaging the pumping plunger (14, 64) and/or the spring element (67) for this purpose.

26. The method according to claim 21, wherein
the cartridge (1, 50) with the ready-mixed cement dough is released from the connecting conduit (38, 44, 88, 94), hollow cylinder (12, 62), and monomer container (46, 96), and the ready-mixed cement dough is dispensed from the internal space (24, 74) of the cartridge (1, 51) by advancing a dispensing plunger (2, 52) that is supported such as to be axially mobile in the cartridge (1, 51) and that bounds the internal space (24, 74) of the cartridge (1, 51) on one side.

27. The device according to claim 11, wherein
the connecting conduit (38, 44, 88, 94) is connected to the hollow cylinder (12, 62) at the lowest point of the hollow cylinder (12, 62), whereby it is optional to have the pumping plunger (14, 64) be arranged on a side opposite of the lower side of the hollow cylinder (12, 62).

28. The device according to claim 14, wherein
the pumping plunger (14, 64) can be pressed axially into the hollow cylinder (12, 62) by hand.

* * * * *